United States Patent [19]
Chandler et al.

[11] Patent Number: 5,895,745
[45] Date of Patent: Apr. 20, 1999

[54] METHOD OF THAWING CRYOPRESERVED CELLS

[75] Inventors: Barbara A. Chandler, Lexington; Kermit M. Borland, Shrewsbury; Shawn P. Cain, North Chelmsford; Claudy J-P. Mullon, Framingham, all of Mass.

[73] Assignee: W.R. Grace & Co.-Conn., Lexington, Mass.

[21] Appl. No.: 08/719,769

[22] Filed: Sep. 25, 1996

[51] Int. Cl.$^6$ .................. A01N 1/02; C12N 5/00; G01N 31/00
[52] U.S. Cl. .................. 435/2; 435/325; 436/18
[58] Field of Search .................. 435/325, 2; 436/18

[56] References Cited

U.S. PATENT DOCUMENTS

| | | | |
|---|---|---|---|
| 4,890,457 | 1/1990 | McNally et al. | 435/325 |
| 5,424,207 | 6/1995 | Carpenter et al. | 435/325 |

FOREIGN PATENT DOCUMENTS

| | | |
|---|---|---|
| 1-157388 | 6/1989 | Japan . |
| WO 88/04889 | 7/1988 | WIPO . |
| WO 92/03046 | 3/1992 | WIPO . |
| WO 96/21351 | 7/1996 | WIPO . |

OTHER PUBLICATIONS

Armitage, Symp. Soc. Exp. Biol., 41:379–393, 1987.
Bald, Cryo Letters, 14(4):207–216, 1993.
Borel Rinkes et al., Cell Transplant, 1(4):281–292, 1992.
Crowe et al., Cryobiology, 26(1):76–84, Feb. 1989.
DeLoecker et al., Cryobiology, 28:237–245, (1991).
Grout et al., Trends Biotechnol., 8(10):293–297, 1990.
Hartmann, Cryo Letters, 8(4):196–203, 1987.
Jochem et al., Warme Und Stoffubertragung–Thermo and Fluid Dynamics, 28:195–204, Mar. 1993.
Kearney, Burns, 17(5):380–383, Oct. 1991.
McGann et al., Cryobiology, 18(5), 469–472, 1981.
Merten et al., Biologicals, 23:185–189, 1995.
Tao et al., J. Reprod. Fertil., 104(2):231–6, Jul. 1995.
Watson, Reproduction Fertility and Development, 7(4):871–891, 1995.

Primary Examiner—Leon B. Lankford, Jr.
Attorney, Agent, or Firm—Fish & Richardson P.C.

[57] ABSTRACT

The invention features a method of processing cryopreserved cells by thawing and equilibrating the cells at warm temperatures (e.g., between 30° C. and 43° C). Either the cell suspension in the cryoprotective medium is thawed to a temperature between 35° C. and 43° C. or the cryoprotective medium is equilibrated with a culture medium at a temperature between 35° C. and 43° C., or both steps are carried out at the warm temperatures. By thawing and equilibrating the cryopreserved cells at warm temperatures, the viability, (especially after 3 hours of culture), and metabolic activity (i.e., diazepam metabolism) of the cells can be improved over traditional cold cell processing (i.e., at temperatures of between 2° C. and 8° C.).

10 Claims, No Drawings

METHOD OF THAWING CRYOPRESERVED CELLS

BACKGROUND OF THE INVENTION

The invention relates to a method of processing cryopreserved cells.

Cells can be preserved in a preservation medium (e.g., cryopreserved) so that they can be recovered alive for later use. For example, mammalian cells such as ova, spermatozoa, hepatocytes, and the like can be successfully cryopreserved. Cryopreservation techniques have been developed and improved over the last decade, however, the thawed cells are typically maintained at low temperatures (i.e., around 4° C.) throughout processing until the cells are needed at full metabolic activity levels. Maintaining and manipulating thawed cells as cold cell suspensions allowed the cells to be manipulated and transported to the site of action without risking loss of activity.

SUMMARY OF THE INVENTION

The invention features a method of processing cryopreserved cells by thawing and equilibrating the cells at warm temperatures (e.g., between 30° C. and 43° C.). Most preferably, either the cell suspension in the cryoprotective medium is thawed to a temperature between 35° C. and 43° C. or the cryoprotective medium is equilibrated by adding a culture medium to dilute the cell suspension at a temperature between 35° C. and 43° C., or both steps are carried out at the warm temperatures. By thawing and equilibrating the cryopreserved cells at warm temperatures, the viability (especially after 3 hours of culture in an incubator), and metabolic activity (e.g., diazepam metabolism) of the cells can be improved over traditional cold cell processing (i.e., at temperatures of about 2° C. to 8° C.).

In one aspect, the invention features a method of recovering cryopreserved cells. The method includes the steps of: thawing frozen cells cryopreserved in a cryoprotective medium to give a first cell suspension; adding a first quantity of culture medium to dilute the first cell suspension; and washing the cells with a fluid selected from either a second culture medium or saline to remove the cryoprotective medium to give a second cell suspension. Either one or both of the thawing and the adding steps are carried out at a temperature between 30° C. and 43° C. Conveniently, the first culture medium and the second culture medium can be the same.

In another aspect, the invention features a method of recovering cryopreserved hepatocytes including the steps of: thawing cryopreserved hepatocytes from a cryoprotective medium to give a hepatocyte suspension; adding a first culture medium to dilute the cryoprotective medium at a temperature between 30° C. and 43° C.; and washing the hepatocytes with a second culture medium or saline by separating the hepatocytes from the cryoprotective medium and adding the culture medium or saline to give a final hepatocyte suspension.

In preferred embodiments, the adding step is carried out between 30° C. and 43° C., more preferably between 35° C. and 43° C. In other preferred embodiments, the thawing step is carried out between 30° C. and 43° C., more preferably between 35° C. and 43° C. Most preferably, both the adding and thawing steps are carried out at between 30° C. and 43° C., more preferably between 35° C. and 43° C.

In preferred embodiments, the cells are mammalian cells, such as hepatocytes, pancreatic islets, chondrocytes, cartilage cells, neural cells, or blood cells. Most preferably, the mammalian cells are hepatocytes.

The washing step can be performed by separating (e.g., centrifuging) the cells from the cryoprotective medium and subsequently adding a culture medium or saline to the cells.

As used herein, "equilibration" or "equilibrating" means adding a culture medium of approximately equal volume to dilute the cell suspension in a protective medium and facilitate removal of the protective medium by lowering the osmolarity of the solution surrounding the cells.

The method of recovering cryopreserved cells can have one or more of the following advantages. Thawing and equilibrating cryopreserved cells (e.g., hepatocytes) at temperatures near 37° C. can result in lower losses of viability and higher cell metabolic rates (e.g., diazepam metabolism). In addition, the cells can exhibit improved cell attachment to substrates, improved survival, and improved cell morphology in comparison to cells thawed by ordinary cold methods. The warm cell thaw and equilibration procedure can increase the yield and function of cryopreserved hepatocytes. In general, hepatocytes that have been thawed and equilibrated at 37° C. show average diazepam function to be 70% of the fresh cell function, whereas hepatocytes thawed and equilibrated to 4° C. could have diazepam metabolism as low as 27% of fresh cell function. Thawing or equilibrating at 37° C. can provide stability to cells, for example, by preventing the cell swelling and mortality that occurs when cryopreserved cells are thawed to 4° C. Warm processed cells can be less swollen and can exhibit less blebbing and fewer ghosts indicating, perhaps, the prevention of injury to the cell membrane which can occur at low temperatures. In addition, warm temperature processing is simplified since the processing temperatures are closer to ambient temperatures.

Other features and advantages of the present invention will be apparent from the following detailed description of the invention, and from the claims.

DETAILED DESCRIPTION

Cryopreserved cells that are equilibrated at a warm temperature between about 30° C. and 43° C. can be rendered substantially free of protective medium. Indeed, cryopreserved cells which are thawed at or near liquid nitrogen temperatures to such warm temperatures prior to the warm equilibration step have improved viability and metabolic activity over time. In general, lower yield, viability, and function for cells recovered by a 4° C. thaw, 4° C. equilibration, and 4° C. wash process are observed in comparison to warm processed cells. Particularly of interest is the 3 hour post thaw viability (cells cultured for 3 hours in a 37° C. incubator), which is significantly lower in the cold processed cells. Cryopreserved hepatocytes recovered by traditional cold processing techniques normally lose approximately 25 to 40% of their post-thaw viability during the first 3 hours of in vitro culture at 37° C. in petri dishes. In contrast, cells recovered by warm equilibration processing lose only about 8% of their post-thaw viability after 3 hours of culture. Any cryopreserved cells that experience an initial thaw or equilibration at a temperature higher than 4° C. have better viability and metabolic activity. Moreover, cells thawed and equilibrated at the higher temperatures have significantly improved viability and performance. The final washing procedure should be carried out with cold saline or media in order to maintain the cells at low metabolic levels until the active cells are needed.

Without further elaboration, it is believed that one skilled in the art can, based on the description herein, utilize the present invention to its fullest extent. All publications cited herein are hereby incorporated by reference. The following specific examples are, therefore, to be construed as merely illustrative, and not limitive of the remainder of the disclosure.

As an example, cryopreserved porcine hepatocytes are recovered from the cryoprotective medium into a viable suspension of cells in a culture medium or saline. The number of cells that are recovered depends upon the use planned for the cells after processing. In the case of use in a bioartificial liver support system, approximately $5 \times 10^9$ viable cells are contained in the vessel. Cryopreserved hepatocytes are described, for example, in Kasai, et al., *Cryobiology*, 30:1-11 (1993).

Thawing of frozen cryopreserved hepatocytes is carried out by immersing a flexible bag (e.g., a Baxter CRYOCYTE bag) containing the cryopreserved cells in a temperature-controlled water bath to give a cell suspension in the protective medium. More specifically, the bags are removed from a freezer at or near liquid nitrogen temperature. Each of the frozen bags contains a volume between approximately 10 mL and 200 mL and contains approximately 1 to $4 \times 10^9$ viable cells. Typically, bags of cryopreserved hepatocytes are thawed simultaneously in the water bath. The water bath used for thawing generally has a capacity of at least 14 L and a heater (e.g., having a power $\geq 30$ W/L) and is maintained at temperatures between about 37° C. and 43° C. The bags containing frozen cells in a cryoprotective medium are immersed in the warm water for approximately 2 minutes depending on volume being thawed. The contents of the bag are warmed to about 35° C. and 43° C. (e.g., 37° C.) in that time.

Once the cell suspension is thawed to a warm temperature in the protective medium, the cells are equilibrated with a culture medium. In this step, the culture medium is introduced into the bag containing the thawed cell suspension in the protective medium. The volume of culture medium added should be approximately equal to the volume of the thawed cell suspension. Culture medium can be introduced into the bag through, for example, a re-sealable port by gravity feeding or an automated cell processor. It is important to avoid introducing foreign contaminants in this step. The culture medium for equilibration is warmed to between about 37° C. and 43° C. before addition to the thawed cell suspension. The equilibration step facilitates the removal of the cryoprotectant in the protective medium from the cell environment by lowering the osmolarity of the solution. Greater than 30 seconds is necessary to allow complete equilibration.

Suitable culture media include Chee's essential medium (CEM), modified eagle medium (MEM), Dulbecco's modified eagle medium (DMEM), Leibowitz's medium, Waymouth's medium, and Kreb's medium. Traditional culture media include additional components such as amino acids or mammalian sera. The preferred culture media for the porcine hepatocytes described herein are CEM and DMEM containing fetal bovine serum (FBS). A protective medium is a culture medium that is supplemented with additives (e.g., the cryoprotectant) so that the cells suspended in it can survive the cryopreservation process. A typical protective medium is a culture medium that includes up to 15%, most preferably 10%, dimethylsulfoxide (DMSO) as the cryoprotectant. A protective medium can also include up to 20% FBS.

Once the cell suspension has been equilibrated with the culture medium in the bag, the cell suspension can be transferred to a cell processor, such as a COBE 2991 cell processor, which includes pumps and tubing for transferring liquids and a centrifuge for washing. The step of washing the cryopreserved hepatocytes can be carried out in the cell processor where the cell suspension that has been thawed is diluted with a culture medium. The cells are substantially separated from the mixture of media using the centrifuge and the substantially cell-free medium is aspirated away from the cell pellet. At this point, the cells are essentially separated from the cryoprotectant. The cell pellet can be further washed with an additional fluid such as culture medium or saline. Conveniently, the culture medium can be the same in the equilibrating and washing steps. More specifically, the fluid is added to the cells, the mixture of cells and fluid is agitated to form a cell suspension, and the cell suspension is centrifuged to give a cell pellet that has been washed. The washing can be repeated multiple times to further remove medium, debris, and cryoprotectant from the cells.

The cells in the cell pellet are then resuspended in a transfer medium to form the transfer cell suspension. The transfer medium can be saline or a culture medium. The transfer cell suspension, being substantially free of cryoprotectant, is transferred out of the cell processor into a vessel.

The preferred vessel is a flexible bag with multiple sealable ports (e.g., a seeding vessel). A sample of the cell suspension can be withdrawn from the vessel in order to count the concentration of cells that are contained in the vessel. The cells are counted using, for example, a hemacytometer. The multiple ports allow the liquid contained in the vessel to be sampled in environmental isolation (i.e., aseptically). The multiple ports also allow samples to be taken for quality control without compromising the integrity of the cell suspension. The total volume of the cell suspension in the vessel can be determined gravimetrically or volumetrically to determine the total number of cells in the vessel. If the number of cells is higher than desired, a weight (or corresponding volume) of the cell suspension that corresponds to the number of cells in excess can be removed. The volume that is removed can be replenished with saline, or another suitable medium, to maintain the total volume of the system. Since all of the manipulations of the cell suspension are carried out aseptically, the cell suspension remains sterile. Hydrated microcarriers can be added aseptically to the hepatocyte suspension, if desired, and the hepatocytes can then be used in artificial liver applications.

The temperature of the medium used for washing depends on when the cells are intended for use. If the recovered cryopreserved cells are to be used immediately, it is sufficient to use warm medium for the washing step(s). In these circumstances, the medium can have temperatures between about 15° C. and 43° C. Alternatively, if it is likely that the cells will not be used immediately (i.e., 1 to 5 hours), the last washing medium should be cold and the washed cells in a culture medium or, especially, in saline, should be stored at or near 4° C. until the active cells are needed (i.e., to treat a patient with an artificial liver support system). The cold medium can have temperatures between about 2° C. and 15° C. (preferably, between 2° C. and 8° C.).

The method of recovering cryopreserved cells was carried out using cryopreserved porcine hepatocytes to compare the effects of equilibrating the cells with culture medium at about 37° C. or thawing the cells to about 37° C. ("warm processing") to the traditional method of thawing and equilibrating cells at 4° C. ("cold processing") as a control. In vitro function of recovered cryopreserved hepatocytes was measured by the ability to metabolize diazepam and cell viability was assessed by trypan blue exclusion with a 1:6 dilution while counting 8 fields per hemacytometer.

The process of cell recovery was carried out in the following manner. The culture medium (DMEM) used in the equilibration step was warmed to about 37° C. by placing it in a suitable environment (e.g. 37° C. to 43° C. water bath or 37° C. to 43° C. incubator) for at least 45 minutes prior to use. Cryocyte bags (100 mL) were removed from liquid or vapor nitrogen storage in a cryo-shipper and immediately submerged in a water bath maintained between 37° C. to 43° C. The bags were gently agitated for 120 seconds. At this point, the cell suspension had thawed and warmed up to a temperature of about 37° C. The thawed bags were removed from the water bath and were aseptically connected to the cell processor (i.e., a Cobe 2991 cell processor, manufactured by Cobe, Lakewood, Calif.). The cell suspension was equilibrated with the warm DMEM. The DMEM was aseptically added to each bag of cells while the bag was being agitated until each bag was approximately half full when thawing 100 mL bags of cells. The bag was visibly red from the addition of the DMEM solution.

After the cell suspension was equilibrated, the cells were washed at a temperature of about 37° C. The equilibrated cell suspension was transferred to a cell processing bag in the centrifuge of the cell processor where the cell suspension was agitated for about 1.25 minutes. The centrifuge was spun at 600 rpm for a period of time long enough to separate the cell pellet from the suspending medium. After spinning for about 1.5 minutes, the supernatant was aspirated away from the cell pellet until the cell pellet remained at the perimeter within the cell processing bag and the supernatant was largely removed. At this point, the cells were resuspended in culture medium.

Cold processing was carried out in an analogous manner, except that the thawing and equilibrating steps were carried out with solutions and suspensions at about 4° C.

Cascade experiments were also carried out to isolate the point in cell processing where exposure to 37° C. leads to improved cell stability and viability. A set of cryopreserved cells was thawed at 4° C. and a second set was thawed at 37° C. Each set was divided into two samples to which warm (37° C.) or cold (4° C.) culture medium was added. Each of the samples was further divided into two batches for warm and cold washing with medium.

After thawing and equilibrating at 4° C. ("cold processing"), the viability of the cells decreased from an initial post thaw viability of 73%, as measured directly after cell recovery, to 50% after 3 hours of in vitro culture. The cells that were recovered by thawing and equilibrating at 37° C. ("warm processing") decreased from 71% post-thaw to only 70% after 3 hours of in vitro culture. In addition, warm processed cells had higher diazepam metabolism, and improved cell attachment, survival, and morphology on vitrogen plates as assessed on day 1 after recovery in comparison to the cold processed cells. Cold processed cryopreserved hepatocytes exhibited diazepam metabolism of 1.41 µg/hr $10^6$ whereas the warm processed cells had diazepam metabolism of 3.16 µg/hr/$10^6$. Thawing at cold temperatures and equilibrating the cells at warm temperatures did not adversely affect the quality of the recovered cells. Cold processed cells demonstrated little attachment, while the cells processed at 37° C. exhibited profoundly greater attachment that permitted cell spreading and formation of plaques of confluent hepatocyte monolayers that differed little from typical fresh cell monolayer cultures.

Furthermore, warm processed cells were less swollen, and exhibited less blebbing and fewer ghosts indicating, perhaps, the prevention of injury to the cell membrane which can occur at low temperatures.

OTHER EMBODIMENTS

From the above description, the essential characteristics of the present invention can be ascertained. Without departing from the spirit and scope thereof, various changes and modifications of the invention can be made to adapt it to various usages and conditions. Thus, other embodiments are also within the claims.

What is claimed is:

1. A method of recovering cryopreserved hepatocytes comprising the steps of:

thawing frozen cryopreserved hepatocytes to give a first hepatocytes suspension at a temperature higher than 4° C. in a cryodrotective medium;

adding a first culture medium to dilute said first hepatocyte suspension; and washing said hepatocytes with a second culture medium or saline to remove said cryoprotective medium to give a second hepatocytes suspension;

wherein one or both of said thawing and said adding steps are carried out at a temperature between 30° C. and 43° C.

2. The method of claim 1, wherein said adding step is carried out between 30° C. and 43° C.

3. The method of claim 2, wherein said thawing step is carried out to give a first hepatocyte suspension at a temperature between 30° C. and 43° C. in a cryoprotective medium.

4. The method of claim 2, wherein said thawing step is carried out to give a first hepatocyte suspension at a temperature between 35° C. and 43° C. in a cryoprotective medium.

5. The method of claim 1, wherein said adding step is carried out between 35° C. and 43° C.

6. The method of claim 5, wherein said thawing step is carried out to give a first hepatocyte suspension at a temperature between 30° C. and 43° C. in a cryoprotective medium.

7. The method of claim 5, wherein said thawing step is carried out to give a first hepatocyte suspension at a temperature between 35° C. and 43° C. in a cryoprotective medium.

8. A method of recovering cryopreserved hepatocytes comprising the steps of:

thawing cryopreserved hepatocytes to give a hepatocyte suspension at a temperature between 30° C. and 43° C. in a cryoprotective medium;

adding a first culture medium to dilute said cryoprotective medium at a temperature between 30° C. and 43° C.; and washing said hepatocytes with a second culture medium or saline by separating said hepatocytes from said cryoprotective medium and adding said second culture medium or saline to give a final hepatocyte suspension.

9. The method of claim 8, wherein said thawing step is carried out to give a hepatocyte suspension at a temperature between 35° C. and 43° C.

10. The method of claim 8, wherein said adding step is carried out between 35° C. and 43° C.

* * * * *